United States Patent [19]

Huey et al.

[11] Patent Number: 4,813,982
[45] Date of Patent: Mar. 21, 1989

[54] PROCESS FOR OBTAINING A BISPHENOL MELT

[75] Inventors: Andrew M. Huey, Lake Jackson, Tex.; Arthur R. Shirley, Jr., Florence, Ala.

[73] Assignee: The Dow Chemical Company, Midland, Mich.

[21] Appl. No.: 5,502

[22] Filed: Jan. 20, 1987

[51] Int. Cl.$^4$ .............................................. B01D 47/00
[52] U.S. Cl. .......................................... 55/80; 55/269; 165/61; 165/111
[58] Field of Search ............... 165/61, 95, 111; 55/82, 55/267, 268, 269, 80; 422/244; 568/724

[56] References Cited

U.S. PATENT DOCUMENTS

| | | | |
|---|---|---|---|
| 1,033,416 | 7/1912 | Kemp et al. | 239/128 |
| 2,898,625 | 8/1959 | Chao | 18/27 |
| 2,955,807 | 10/1960 | Riley et al. | 165/61 |
| 3,084,914 | 4/1963 | Davis | 165/61 |
| 3,231,413 | 1/1966 | Berquin | 117/100 |
| 3,255,036 | 6/1966 | Kramer et al. | 117/100 |
| 3,556,403 | 1/1971 | Manginelli | 239/135 |
| 3,579,721 | 5/1971 | Kaltenbach | 18/27 |
| 3,711,254 | 1/1973 | McGowan | 23/313 |
| 3,791,110 | 2/1974 | Klan et al. | 55/82 X |
| 3,867,410 | 2/1975 | Brand et al. | 165/61 X |
| 3,869,479 | 3/1975 | Barth et al. | 165/61 X |
| 3,877,415 | 4/1975 | Blouin | 118/303 |
| 3,960,968 | 6/1976 | Vernaleken et al. | 568/723 |
| 3,991,225 | 11/1976 | Blouin | 427/3 |
| 4,002,198 | 1/1977 | Wagner et al. | 165/61 |
| 4,133,290 | 1/1979 | Melliger | 118/7 |
| 4,160,110 | 7/1979 | Carnahan, Jr. | 568/703 |
| 4,190,622 | 2/1980 | Landis | 264/14 |
| 4,213,924 | 7/1980 | Shirley, Jr. | 264/7 |
| 4,252,772 | 2/1981 | Way | 165/61 X |
| 4,272,234 | 6/1981 | Tse | 425/222 |
| 4,353,852 | 10/1981 | Tse | 264/37 |
| 4,370,501 | 1/1983 | Lau | 564/330 |
| 4,424,176 | 1/1984 | Shirley, Jr. et al. | 264/7 |
| 4,440,866 | 4/1984 | Lunghofer et al. | 501/127 |
| 4,506,453 | 3/1985 | Shirley, Jr. et al. | 34/12 |
| 4,507,335 | 3/1985 | Mathur | 427/215 |
| 4,720,596 | 1/1988 | Kissinger et al. | 568/724 |

FOREIGN PATENT DOCUMENTS 83024292  1/1982  Fed. Rep. of Germany .

OTHER PUBLICATIONS

U.S. patent application Ser. No. 005,507, filed 1-20-87 by Andrew M. Huey et al., entitled PROCESS AND APPARATUS FOR PRODUCING PRILLS.
U.S. patent application Ser. No. 005,505, filed 1-20-87 by Andrew Michael Huey et al., entitled SPRAY HEADER AND NOZZLE ASSEMBLY.
U.S. patent application Ser. No. 005,504, filed 1-20-87 by Kenneth T. McDonald et al., entitled PRODUCTION OF GRANULAR BISPHENOLS.
U.S. patent application Ser. No. 005,503, filed 1-20-87 by Andrew M. Huey et al., entitled DUST COLLECTION ASSEMBLY.

Primary Examiner—Ira S. Lazarus
Assistant Examiner—Richard R. Cole

[57] ABSTRACT

A process of removing dust collected on the internal surfaces of a shell and tube type heat exchanger after passing a dust containing gas stream through the shell-side of a heat exchanger, by passing a heating fluid through the tube-side of the heat exchanger at a temperature sufficient to melt the dust particles, and collecting the melt at the bottom most portion of the heat exchanger in a melt collection device such as a pan or container.

2 Claims, 1 Drawing Sheet

PROCESS FOR OBTAINING A BISPHENOL MELT

BACKGROUND OF THE INVENTION

This invention relates to a process for removing meltable dust collected on internal surfaces of a heat exchanger.

There is a wide variety of heat exchangers used in many industrial processes. For example, heat exchangers used for cooling gas streams include a shell and tube-type exchanger wherein the gas stream is cooled by flowing a cooling medium in the tube-side of the exchanger and flowing the gas stream in the shell-side of the exchanger.

In processes where the gas stream has collected dust particles, the dust particles can deposit themselves on the outside surfaces of the tubes in the exchanger and the inside surfaces of the shell of the exchanger reducing the efficiency of the exchanger. In order to clean out the exchanger and remove the dust off of the tubes, a shut down of the process is necessary. A great amount of time can be consumed in having an operator clean out the heat exchanger manually.

It is therefore desired to provide a novel process for removing dust particles that are deposited on the internal surfaces of heat exchangers.

SUMMARY OF THE INVENTION

This invention is directed to a process of removing meltable dust collected on internal surfaces of a shell and tube type heat exchanger by passing a heating fluid through the tube-side of the heat exchanger at a temperature sufficient to melt the dust particles on the outside surface of the tubes and the internal surfaces of the shell, and collecting the melt at the bottom most portion of the heat exchanger in a melt collection device such as a pan or container.

DETAILED DESCRIPTION OF THE PREFERRED EMBODIMENTS

Figure 1:
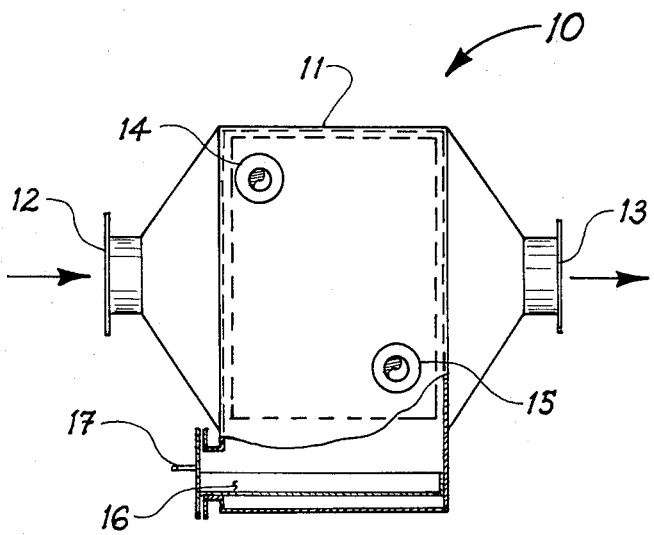
FIG. 1 is a front, partially cut away view showing a heat exchanger useful in the present invention.

With reference to FIG. 1, there is shown the heat exchanger of the present invention, generally indicated by numeral 10 including an enclosure or housing (shell) 11 with an inlet 12 and outlet 13 for feeding a gaseous stream therethrough. The housing 11 contains a plurality of tubes or tube bundle (not shown) for passing a fluid medium therethrough. A tube bundle inlet 14 and a tube bundle outlet 15 are used for passing a fluid medium such as a coolant or heating fluid through the tube bundle. The tube bundle preferably used are the finned type known in the art.

A unique feature of the present heat exchanger is a removable melt collection tray 16 with handles 17 disposed at the bottommost portion of the heat exchanger 10. The tray is preferably slidably and removably mounted on the heat exchanger. The tray is used for collecting melt which has been allowed to fall by gravity onto the tray. The heat exchanger is therefore cleaned out by removing the tray containing the melt after a predetermined period of operation.

As another embodiment of the present invention, the tray 16 can be a non-removable tray provided with a heating means (not shown) for monitoring the melt in a molten or liquid state. The melt can then be removed in the liquid state by drawing the melt using a drain means (not shown) to a meltable point.

Figure 2:
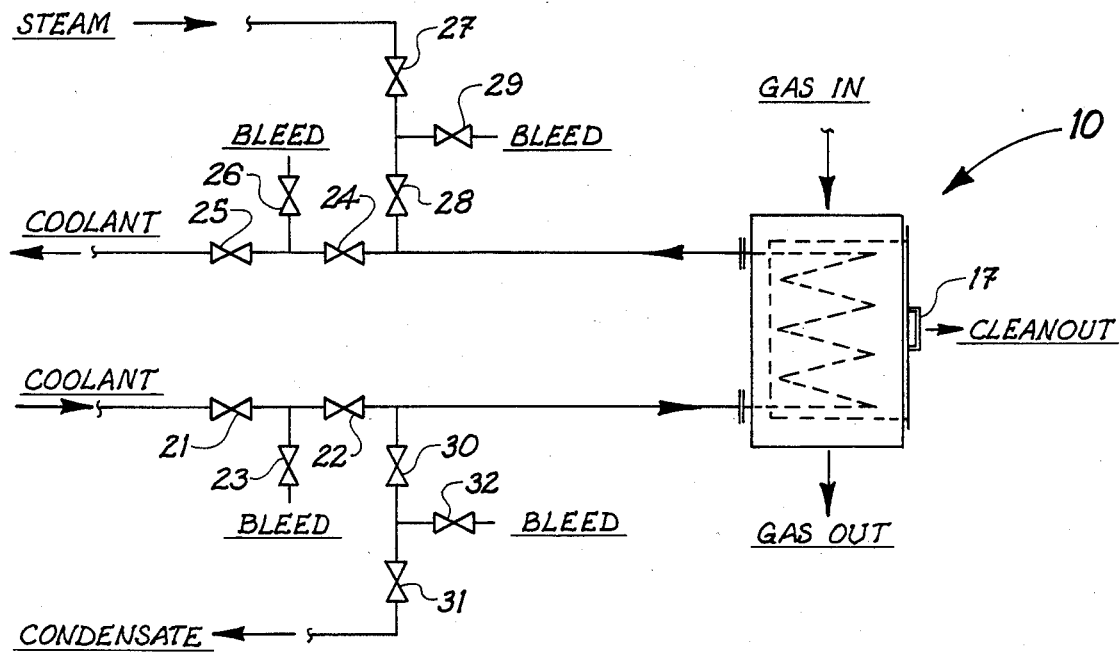
FIG. 2 is a schematic flow diagram of the process of the present invention.

With reference to FIG. 2, there is shown a heat exchanger with a valve system for carrying out the preferred process of the present invention wherein a gas containing dust particles is passed through the shell-side of the exchanger. The dust particles in the gas stream settle on the outside surfaces of the tubes and on the internal surfaces of the shell of the heat exchanger.

The series of valves shown in FIG. 2 is used to control the flow of coolant or heating fluid to the exchanger depending on whether the gas is to be cooled or the meltable dust particles are to be removed from the outside surfaces of the tubes in the heat exchanger. For example, for feeding coolant to the exchanger, valves 21-26 are opened and valves 27-32 are closed off. Valves 23 and 26 are bleed valves for removing excess fluid and can be closed initially and intermittently opened.

When dust particles are to be removed from the gas stream, for example, valves 21-16 are closed off and valves 27-32 are opened to feed a heating fluid such as steam to heat the tube surfaces to melt the dust particles deposited on the heat exchanger's internal surfaces. Valves 29 and 32 are bleed valves and can be initially closed and intermittently opened to remove excess fluid.

The present invention is useful in processes in which a gaseous stream comes into contact with dust particles and carries at least a portion of the dust particles to downstream processing equipment. The dust particles contained in the gas stream are those that can be melted at an elevated temperature. For example, bisphenol, normally, is a solid or semisolid at ambient temperatures but can be reduced to a liquid state by melting and can be returned to the solid or semisolid state by cooling below the melt temperature.

As an illustration only and not to be limited thereby, U.S. patent application Ser. No. 005,504, entitled "Production of Granular Bisphenol", filed of even date herewith, in the names of Kenneth T. McDonald and Arthur R. Shirley, incorporated herein by reference, describes a process wherein the present invention is useful. The process includes using an inert gas such as nitrogen to cool molten bisphenol in a granulation drum and thereafter cooling the heated nitrogen in an exchanger prior to recycling the nitrogen back into the granulation drum. In the granulation drum, a high level of dust is formed and is carried out by the nitrogen passed through the drum. When the nitrogen is sent to a cooling means such as a shell and tube-type heat exchanger, the dust particles can be deposited on the internal surfaces of the exchanger.

Herein, the present invention will be described with reference to the production of bisphenols by using the drum granulation process above, but it is understood that the invention is not limited thereto. The present invention can be used in any process requiring meltable dust removed from a heat exchanger.

The process for producing a bisphenol granules includes feeding a seed material of bisphenol into a rotary granulation drum, preferably enclosed in a gas-tight housing and spraying molten bisphenol onto the seed material in the presence of an inert gaseous atmosphere such as nitrogen. The required size of the product granules is formed by layering molten bisphenol by the spray action of molten bisphenol directly onto seed material.

The seed particles of bisphenols fed into the drum granulator are produced by any conventional seed generating system, for example, using conventional crushing or milling equipment.

The rotary granulation drum used in the present invention can be of the type described in U.S. Pat. Nos. 3,877,415; 3,991,225; 4,213,924; 4,424,176 and 4,506,453. Generally, the rotary drum is equipped with longitudinal lifting vanes, or flights, preferably equally spaced on the drums inside shell and specially designed to form continuous longitudinal curtains of falling solid particles as the drum rotates. The shower of falling solid particles formed by the movement of the lifting flights fall on a deflector pan or pans for providing a curtain of falling granules on which the molten material can be sprayed.

As the drum rotates, the seed particles and recycle undersized granules are elevated from the bed by the lifting flights and dropped onto preferably, two inclined collecting pans installed in a step fashion. Granules flowing from the top pan onto the bottom pan form an upper curtain and granules flowing form the bottom pan form a dense bottom curtain. Molten bisphenol is preferably sprayed on the lower curtain of the falling granules. Spraying of molten bisphenols onto the falling granules is carried out using a plurality of spray nozzles supported in a steam jacketed header assembly. The steam jacketed spray header is used to maintain the temperature of the melt. The melt is preferably maintained at a temperature of from about 154° C. to about 160° C. and the beads inside the drum the preferably maintained at a temperature of about 70° C. to about 138° C. and more preferably from about 123° C. to about 130° C. The spray pattern is linear with each nozzle rotated slightly off the horizontal to avoid over lapping spray streams.

Preferably, the nozzles used in the present invention form a fully atomized spray wherein the droplets of molten bisphenols are atomized finely enough such that the formation of agglomerates in the granulation drum is minimized. The nozzles used to form the finely atomized spray are preferably pressure-atomizing nozzles, i.e., nozzles in which the liquid is propelled by its own pressure through a small orifice at such high velocity that the stream is broken down into small droplets. The finely atomized bisphenols melt forms a thin layer on the falling granules and quickly solidifies on the relatively cool surface. Product granules of the desired size are formed by successive layering of the melt on the granules as they pass through the drum.

As the sprayed bisphenols solidifies on the undersize granules, considerable heat is released into the granulation drum. Cooling is provided by the nitrogen gas stream being directed through the upper curtain of falling granules through gas distributors, thus providing an efficient process of heat exchange between the hot granules and the cooled gas stream.

The nitrogen gas stream is passed from a blower to the gas distributor inside the granulator drum. A nitrogen gas collection header inside the drum is used to pull the nitrogen from the drum to a dust removal means. Dust produced in the granulation drum which exits the drum with the nitrogen gaseous stream can be separated from the gas and collected by conventional equipment known in the art, for example, in a cyclone separator or bag house filters. The dust collected from the dust removal means may be remelted and the melt may be recycled to the melt bisphenol feed stream to the drum granulator or the melt may be sent to a use point.

Preferably, the nitrogen stream from the dust removal system is cooled, for example, in a conventional shell and tube-type heat exchanger using cooling tower water as the cooling medium. Then the nitrogen can be recycled back to the granulator after passing through the cooler.

Often, the dust removal means can not remove completely the dust contained in the gas stream passing to the cooler and after a period of time, dust builds up inside the cooler until the efficiency of the cooler is unsatisfactory. Thus, the cooler must be cleaned of dust build up. The system of the present invention is advantageously used in this instance.

Granules discharge from the drum granulator into a double deck screen for separating the product from oversize and undersize granules. The onsize or product granules of bisphenols are routed from the screen to, for example, bulk storage, to a fluid bed cooler for further cooling, or to a desired use point. The oversize from the screen may be remelted in a melter and recycled or fed into the granulator with the molten bisphenol feed stream, or conveyed to a desired use point. Optionally, the oversize may be ground for use as seed material. The undersize from the screen is conveyed to a recycle hopper, where it is fed back into the granulation drum with seed material at a metered rate by a weigh feeder. Optionally, the undersize may be fed into the melter for recycling or conveyed to another desired use point.

What is claimed is:

1. A process for removing bisphenol meltable dust collected on the internal surfaces of a shell and tube type heat exchanger used in a process for producing bisphenol granules comprising:
   a. passing an inert gas containing bisphenol dust particles through the shell side of said heat exchanger and allowing the bisphenol dust particles to settle on the tubes of said heat exchanger;
   b. passing heated fluid medium through the tube side of the heat exchanger at a temperature sufficient to melt the bisphenol dust particles on the outside surfaces of the tubes and the internal surfaces of the shell of the heat exchanger and forming a bisphenol melt;
   c. allowing the bisphenol melt to fall by gravitational forces from the surfaces of said heat exchanger;
   d. collecting the fallen melt below the heat exchanger; and
   e. removing the bisphenol melt from the heat exchanger.

2. A process for separating bisphenol dust particles from an inert gaseous stream passing through a shell and tube type heat exchanger used in a process for producing bisphenol granules and removing bisphenol dust particles deposited on the outside surfaces of the tubes and the internal surfaces of the shell of the heat exchanger comprising:
   a. passing an inert gas stream containing bisphenol dust particles through the shell side of the heat exchanger while passing a cooling fluid medium through the tube side of the heat exchanger for a predetermined period such that the bisphenol dust particles settle on the outside surfaces of the tubes and the internal surfaces of the shell of the heat exchanger;

b. closing off the flow of cooling fluid medium through the tube side of the heat exchanger and passing heated fluid medium through the tube side of the heat exchanger at a temperature sufficient to melt the bisphenol dust particles on the outside surfaces of the tubes and the internal surfaces of the shell of the heat exchanger and forming a bisphenol melt;

c. allowing the bisphenol melt to fall by gravitational forces from the surfaces of said heat exchanger;

d. collecting the fallen bisphenol melt below the heat exchanger; and e. removing the bisphenol melt from the heat exchanger after a predetermined period of heat exchanger operation.

* * * * *

UNITED STATES PATENT AND TRADEMARK OFFICE
CERTIFICATE OF CORRECTION

PATENT NO. : 4,813,982

DATED : March 21, 1989

INVENTOR(S) : Huey et al.

It is certified that error appears in the above-identified patent and that said Letters Patent is hereby corrected as shown below:

Col. 2, line 23; change "16" to --26--.

Col. 2, line 63; delete the "a" between "producing" and "bisphenol".

Col. 3, line 34; change "the" between "drum" and "preferably" to --are--.

Signed and Sealed this

Thirty-first Day of July, 1990

Attest:

HARRY F. MANBECK, JR.

*Attesting Officer*　　　　　　　*Commissioner of Patents and Trademarks*